United States Patent
Lee et al.

(10) Patent No.: US 8,124,311 B2
(45) Date of Patent: Feb. 28, 2012

(54) PHOTOSENSITIVE MOLECULAR COMPOUND AND PHOTORESIST COMPOSITION INCLUDING THE SAME

(75) Inventors: Jung-Youl Lee, Anyang-Si (KR);
Jeong-Sik Kim, Hwaseon-Si (KR);
Eu-Jean Jang, Hwaseong-Si (KR);
Jae-Woo Lee, Bucheon-Si (KR);
Jae-Hyun Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 227 days.

(21) Appl. No.: 12/361,833

(22) Filed: Jan. 29, 2009

(65) Prior Publication Data
US 2009/0197198 A1    Aug. 6, 2009

(30) Foreign Application Priority Data
Jan. 30, 2008   (KR) .................. 10-2008-0009597

(51) Int. Cl.
G03F 7/039 (2006.01)
G03F 7/20 (2006.01)
G03F 7/30 (2006.01)
G03F 7/38 (2006.01)

(52) U.S. Cl. ............ 430/270.1; 430/326; 430/330; 564/254; 548/473; 548/440; 546/98

(58) Field of Classification Search .............. None
See application file for complete search history.

(56) References Cited

OTHER PUBLICATIONS

Sansone et al ("Synthesis and Structure of Chiral Cone Calix[4]arenes Functionalized at the Upper Rim with L-Alanine Units", European Journal of Organic Chemistry vol. 1998, Issue 5 (1998), pp. 897-905).*

* cited by examiner

Primary Examiner — Sin J. Lee
(74) Attorney, Agent, or Firm — Birch, Stewart, Kolasch & Birch, LLP

(57) ABSTRACT

Disclosed are a photosensitive compound containing oxime group which is directly decomposed by exposure to light, which is a molecular resist whose size is smaller than conventional polymer for photoresist, and a photoresist composition including the same. The photosensitive molecular compound has a structure represented by a following formula.

[Formula]

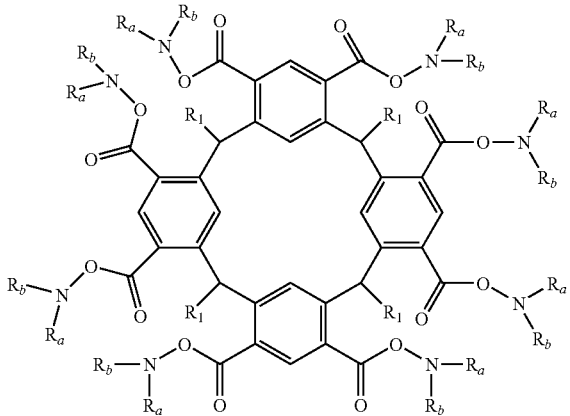

In Formula, $R_1$ is hydrogen atom or methyl group ($CH_3$); $R_a$ and $R_b$ each is independently alkyl group of 1-6 carbon atoms, alkylcarbonyl group of 2-7 carbon atoms, aryl group of 6-10 carbon atoms or arylcarbonyl group of 7-11 carbon atoms, and $R_a$ and $R_b$ form one group as an united body, alkyl or cycloalkyl group of 1-20 carbon atoms or arylalkyl group of 7-20 carbon atoms which are doubly bonded to nitrogen atom.

7 Claims, No Drawings

PHOTOSENSITIVE MOLECULAR COMPOUND AND PHOTORESIST COMPOSITION INCLUDING THE SAME

This application claims the priority benefit of Korean Patent Application No. 10-2008-0009597 filed on Jan. 30, 2008. All disclosure of the Korean Patent application is incorporated herein by reference.

FIELD OF THE INVENTION

This invention relates to a photosensitive molecular compound and a photoresist composition including the same, and more particularly to a photosensitive molecular compound containing oxime group which is directly decomposed by exposure to light, which is a molecular resist whose size is smaller than conventional polymer for photoresist, and a photoresist composition including the same.

BACKGROUNDS OF THE INVENTION

The photolithography is a process used to form a circuit pattern of a semiconductor chip or a display element from a semiconductor wafer or a glass for the display element. The photoresist composition is the most essential materials to the photolithography process. Recently, as the patterns for semiconductor devices and the display elements are finer, the need for the photoresist composition having high resolution is more increased.

Conventional acid-amplified photoresist composition includes a polymer resin, a photo-acid generator (PAG), an organic solvent and a base compound as occasion demands. Since the conventional photoresist composition includes the polymer resin as a main component, it has excellent mechanical properties such as processability, coating stability, etching resistance and can be easily removed after the succeeding process including an etching process, an ion implantation process and so on. However, it has disadvantage in that the resolution of photoresist composition is restricted by the size of polymer resin. Therefore, a photoresist composition using a molecular resist instead of large-sized polymer resin, has been developed.

The chemically-amplified photoresist composition uses a chemical amplifier reaction (CAR) of an acid diffusion and a deprotection of protecting group due to the acid component. Specifically, in case where the photosensitive molecular compound is used for the chemically-amplified photoresist composition, the most deprotection of the protecting group is created by the CAR. In the CAR, a PEB (post exposure bake) causes the elimination and diffusion of the acid at an exposure region, so the diffusion length of acid varies according to a temperature of the PEB. As the diffusion length of acid is longer, the resolution of photoresist pattern decreases. Accordingly, for improving the resolution of photoresist pattern, it is necessary to use a compound with a short acid-diffusion length or a compound whose solubility with respect to a developing solution varies without an acid-diffusion step.

SUMMARY OF THE INVENTION

Therefore, it is an object of the present invention to provide a photosensitive molecular compound having an oxime group which is directly decomposed by exposure to light so that solubility thereof to a developing solution varies without an acid-diffusion step, and a photoresist composition including the same.

It is another object of the present invention to provide a photosensitive molecular compound which can improve resolution of lithography process, and has an advanced line edge roughness (LER), and can improve uniformity of layer after coating or forming pattern, and a photoresist composition including the same.

In order to achieve these objects, the present invention provides a photosensitive molecular compound having a structure of following Formula 1.

[Formula 1]

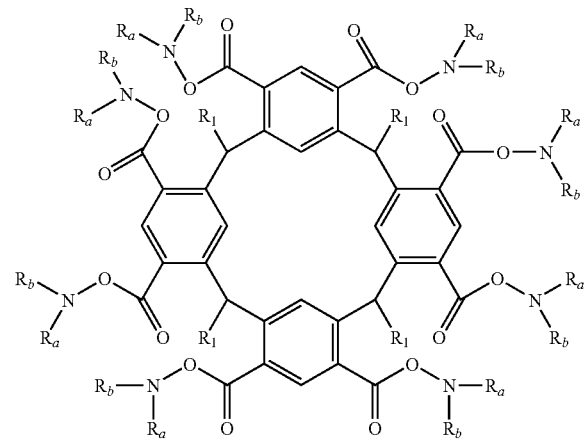

In Formula 1, $R_1$ is hydrogen atom or methyl group ($CH_3$), $R_a$ and $R_b$ each is independently alkyl group of 1-6 carbon atoms, alkylcarbonyl group of 2-7 carbon atoms, aryl group of 6-10 carbon atoms or arylcarbonyl group of 7-11 carbon atoms, and $R_a$ and $R_b$ form one group as an united body, alkyl or cycloalkyl group of 1-20 carbon atoms or arylalkyl group of 7-20 carbon atoms which are doubly bonded to nitrogen atom.

The present invention also provides a photoresist composition comprising 1 to 85 wt % (weight %) of the photosensitive molecular compound; and a remaining organic solvent. The present invention also provides a method for forming photoresist pattern composition comprising the step of: (a) coating a photoresist composition containing a photosensitive molecular compound on a substrate to form a photoresist layer; (b) exposing the photoresist layer to a light; (c) heating the exposed photoresist layer; and (d) developing the heated photoresist layer to form the photoresist pattern.

The photosensitive molecular compound of the present invention is decomposed by a light, so the solubility thereof with respect to a developing solution varies even without an acid diffusion. Thus a resolution of lithography process and a line edge roughness (LER) are improved and also a uniformity of layer after coating or forming pattern is enhanced.

DETAILED DESCRIPTION OF THE INVENTION

A more complete appreciation of the invention, and many of the attendant advantages thereof, will be better appreciated by reference to the following detailed description.

The photosensitive molecular compound according to the present invention is a compound containing an oxime structure and has a structure of following Formula 1. In the present photosensitive molecular compound, the deprotection of the oxime structure is made by the exposure to light, and the solubility thereof with respect to the developing solution varies.

[Formula 1]

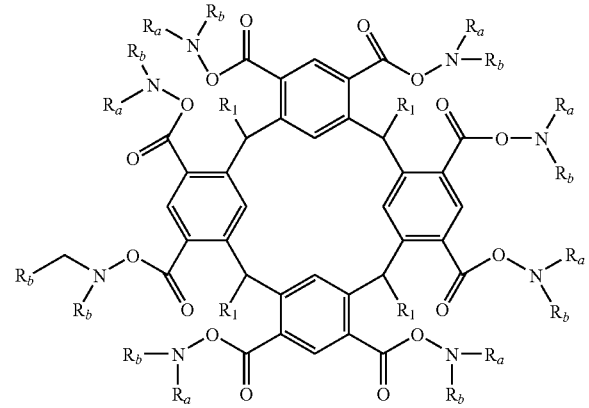

In Formula 1, $R_1$ is hydrogen atom or methyl group ($CH_3$), $R_a$ and $R_b$ each is independently alkyl group of 1-6 carbon atoms, preferably 1-3 carbon atoms, alkylcarbonyl group of 2-7 carbon atoms, aryl group of 6-10 carbon atoms or arylcarbonyl group of 7-11 carbon atoms, and $R_a$ and $R_b$ form one group as an united body, alkyl or cycloalkyl group of 1-20 carbon atoms or arylalkyl group of 7-20 carbon atoms which are doubly bonded to nitrogen atom. $R_a$ and $R_b$ may be coupled to each other to form a ring structure.

The representative examples of the photosensitive molecular compound represented by the Formula 1 include compounds represented by the following Formulas 2a to 2g.

[Formula 2a]

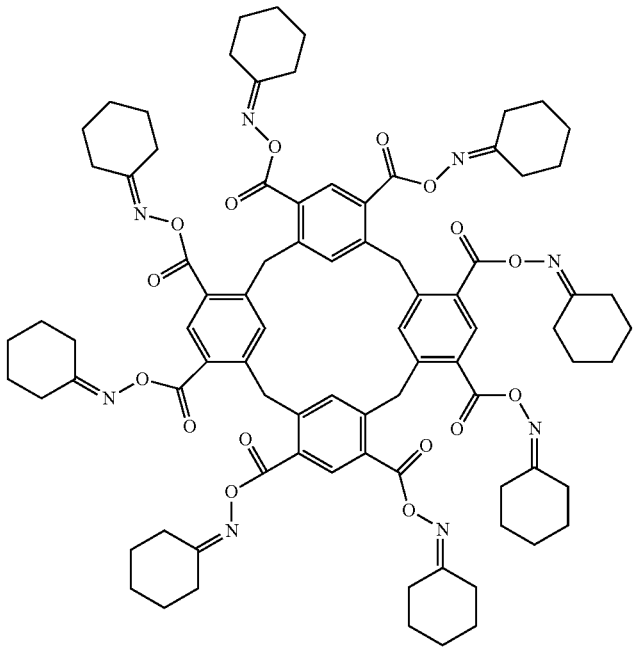

[Formula 2b]

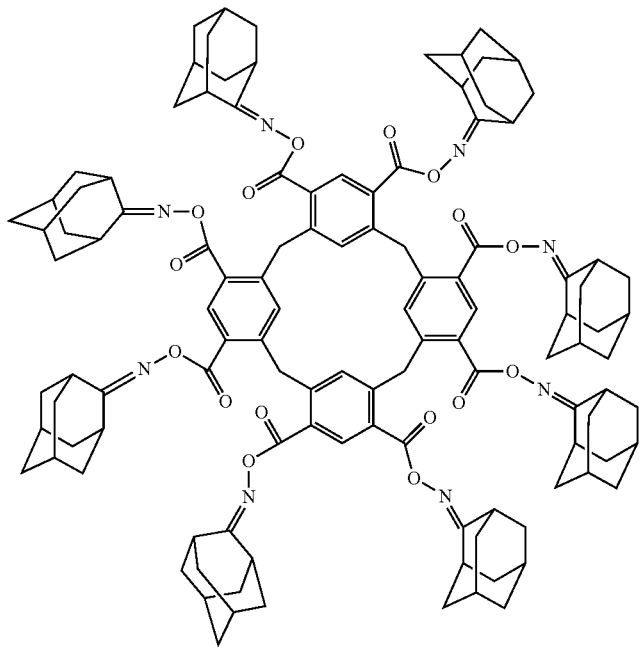

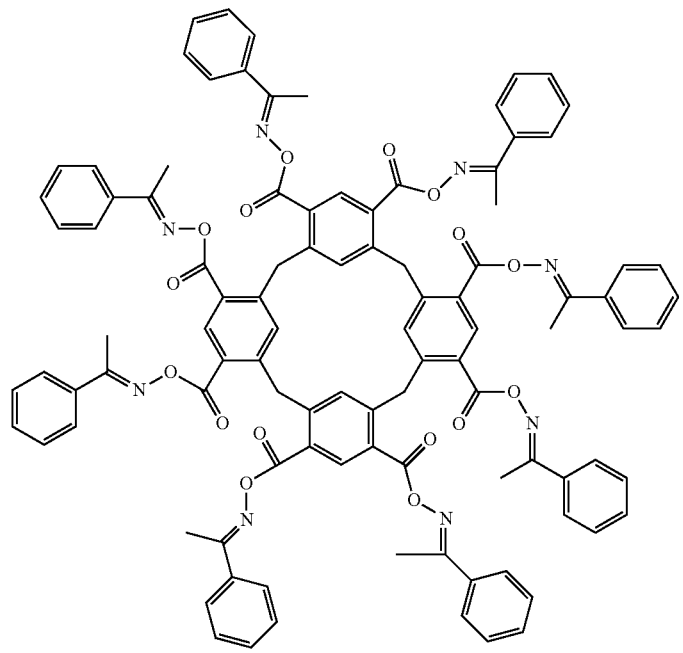
[Formula 2c]
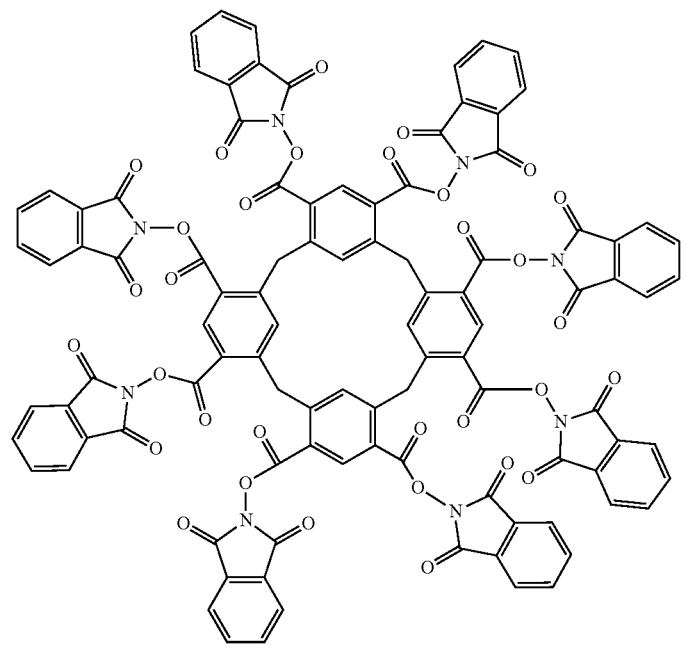
[Formula 2d]

[Formula 2e]
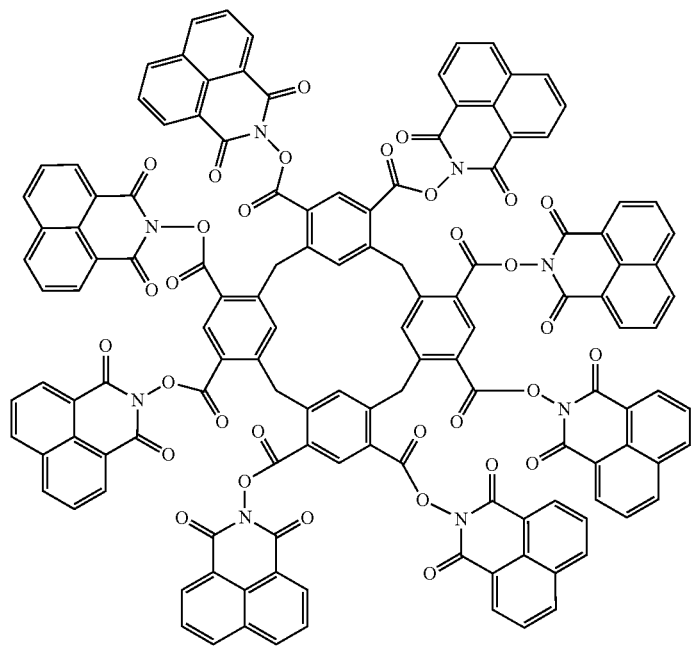
[Formula 2f]
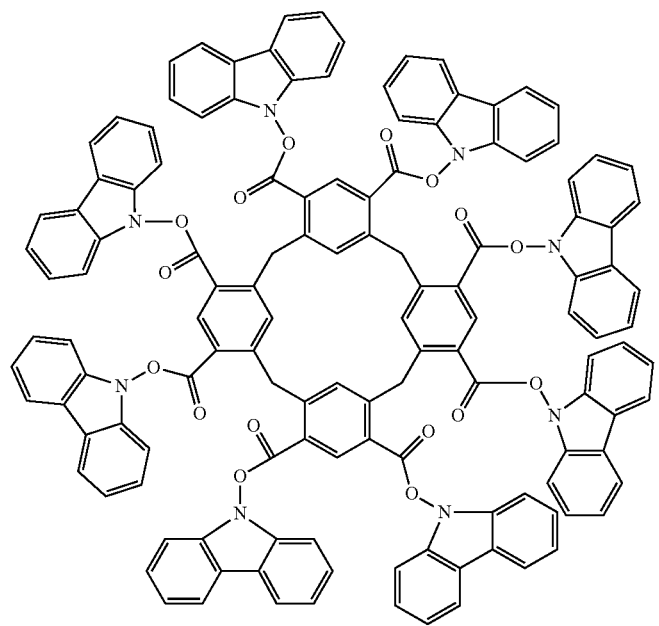

[Formula 2g]

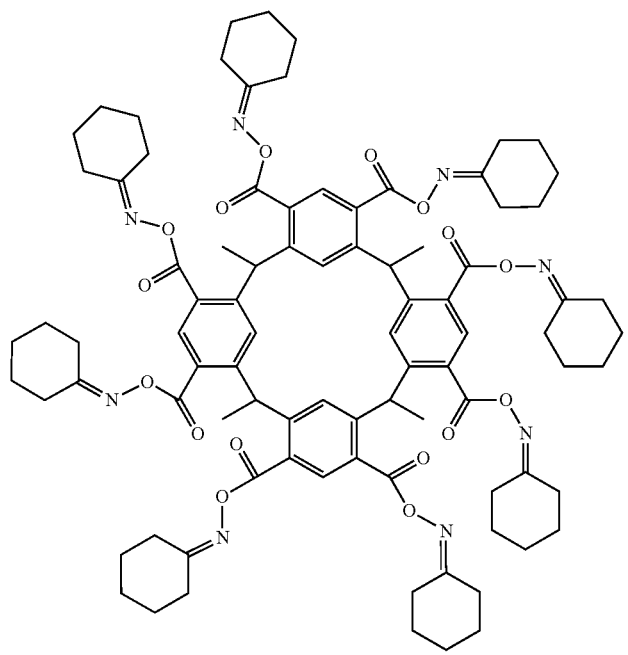

In the lithography process, the oxime group of the photosensitive molecular compound according to the present invention, even if there is no a PAG, is decomposed by the exposure to light, and the solubility thereof with respect to the developing solution is changed to form photoresist patterns. In addition, the photosensitive molecular compound has a small unit structure and low polydispersity compared with the photosensitive polymer. Accordingly, if the photosensitive molecular compound is used, LER of the photoresist pattern is reduced, and also since an influence of the acid-diffusion is reduced during the PEB process, decreased are PEB sensitivity, PCD (Post-Coating Delay) sensitivity and PED (Post exposure delay) due to the difference of the exposure time at the same wafers.

The photosensitive molecular compound of the present invention can be synthesized by conventional organic synthesis methods. For example, as shown in following Reaction 1, an intermediate of ring compound of Formula 3 is prepared by a reaction of benzene derivatives compound and aldehyde compound at 90° C. under an acid catalyst. Then the impurities were removed by washing the reaction solution with water several times.

[Reaction 1]

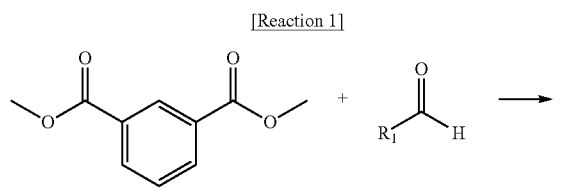

-continued

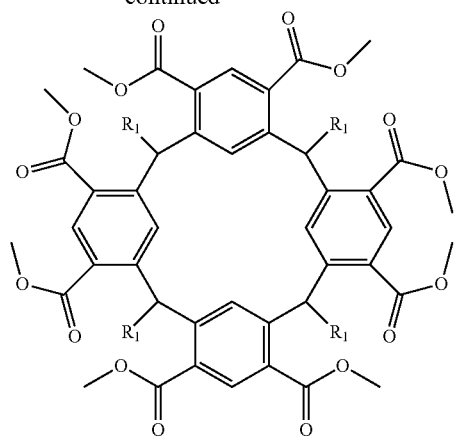

Formula 3

Next, as shown in following Reaction 2, the compound obtained in Reaction 1 is reacted with aqueous NaOH saturated solution for 24 hours at 40° C. and the reactant is washed with water several times to prepare an intermediate of Formula 4.

[Reaction 2]

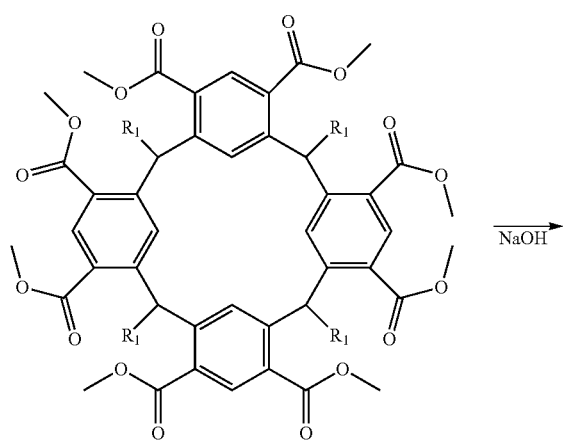

→ NaOH

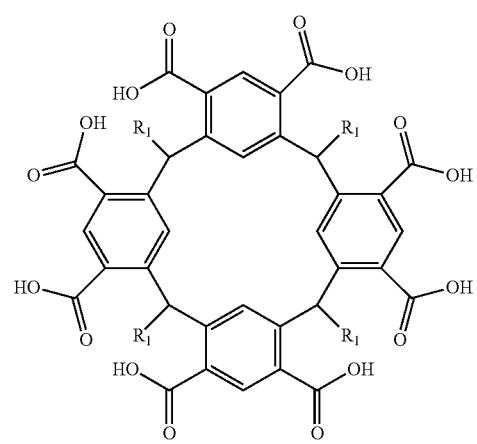

Formula 4

Then, as shown in following Reaction 3, the compound obtained in Reaction 2 is dissolved in tetrahydrofuran (THF) anhydride and then reacted with thionyl chloride at 0° C. After completing the reaction, the product is washed with water and refined to obtain an intermediate of Formula 5.

[Reaction 3]

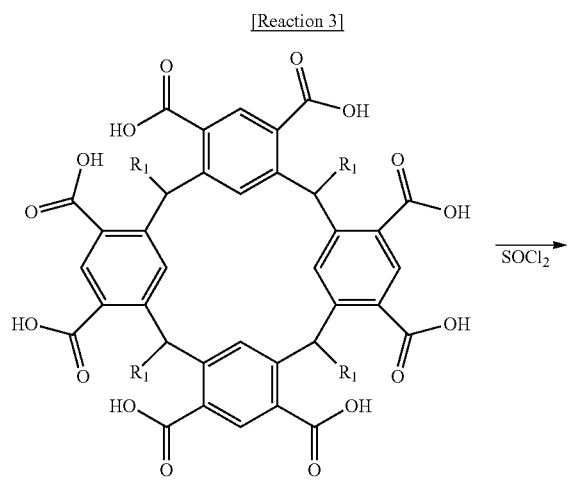

→ $SOCl_2$

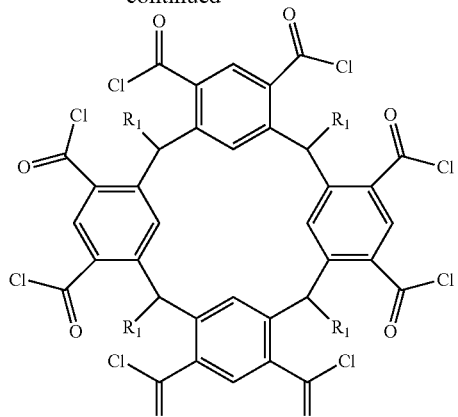

Formula 5

Finally, as shown in following Reaction 4, the compound obtained in the Reaction 3 is reacted with an oxime derivatives compound at room temperature and the product is washed with water several times for removing the initial impurities, to obtain the photosensitive molecular compound of Formula 1 according to the present invention.

[Reaction 4]

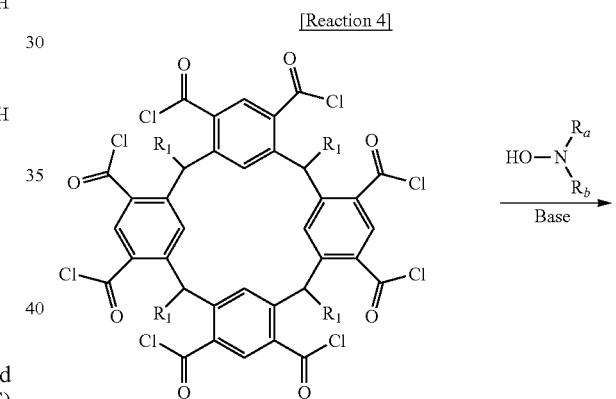

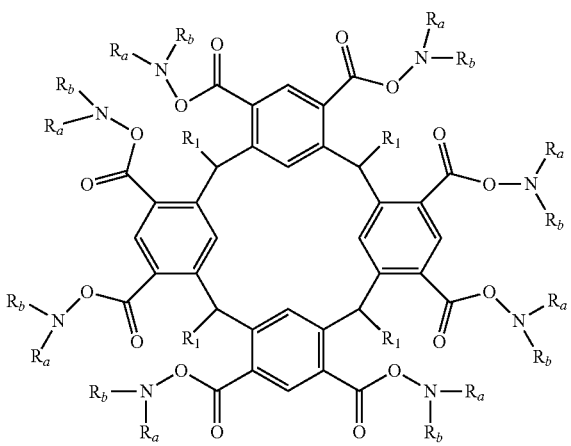

Formula 1

In the preparation of the photosensitive molecular compound, the examples of aldehyde compound reacting with benzene derivatives

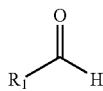
(Formula 7)

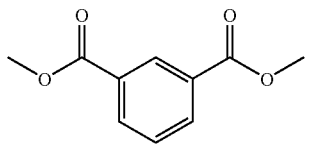
(Formula 6)

of Reaction 1 include

(Formula 7a)

or

(Formula 7b)

and examples of oxime derivatives compound of Reaction 4 include

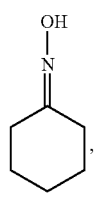
(Formula 8a)

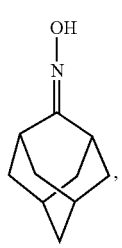
(Formula 8b)

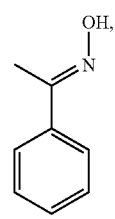
(Formula 8c)

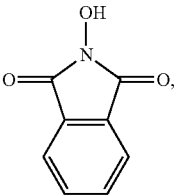
(Formula 8d)

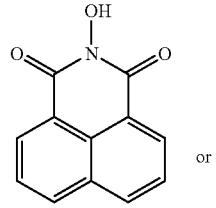
(Formula 8e)

or

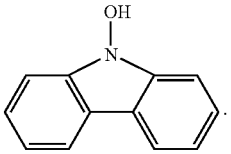
(Formula 8f)

The photoresist composition according to the present invention includes the photosensitive molecular compound represented by the Formula 1 and an organic solvent, and, if necessary, further includes a base compound as a quencher, and a surfactant. In the photoresist composition, the amount of the photosensitive molecular compound is 1 to 85 wt % (weight %), preferably 2 to 45 wt %, more preferably 3 to 25 wt %, and the reminder is of the organic solvent. The amount of the organic solvent is 180 to 5000 weight part, preferably 400 to 3000 weight part with respect to 100 weight part of the photosensitive molecular compound. Wherein, if the amount of the photosensitive molecular compound is too little (less than 1 wt %), it is difficult to form the photoresist layer with a desired thickness. If the amount of the photosensitive molecular compound is too much (more than 85 wt %), the thickness of patterns formed on the wafer may be not uniform.

Also, if necessary, the photosensitive composition according to the present invention further comprises a conventional photosensitive polymer for the photoresist which reacts with an acid and then whose solubility to a developer is changed, within the limits not to disturb the function of the photosensitive molecular compound of the present invention. The photosensitive polymer may be block copolymer or random copolymer having a protecting group sensitive to acid, and the weight average molecular weight (Mw) of conventional photosensitive polymer is preferably 3,000 to 20,000. The amount of the conventional photosensitive polymer, if used, is 1 to 30 wt %, preferably 5 to 25 wt % with respect to total photoresist composition of the present invention. If the amount of the conventional photosensitive polymer is less than 1 wt %, the effect of the photoresist polymer cannot be obtained, and if the amount of the conventional photosensitive polymer is more than 30 wt %, a coating uniformity may be degraded. When the conventional photosensitive polymer is used, the conventional PAG also can be contained in the photosensitive composition of the present invention. The amount of the PAG, if used, is 0.05 to 30 weight part, preferably 0.15 to 10 weight part with respect to 100 weight part of the conventional photosensitive polymer. If the amount of the PAG is too little (less than 0.05 weight parts), the light sensitivity of the photoresist composition may decrease. If the amount of the PAG is too much (more than 30 weight parts), the profile of the photoresist patterns may be deteriorated because the PAG absorbs a lot of ultraviolet rays and a large quantity of acid is produced from the PAG.

As the PAG (photo-acid generator), any conventional PAG which can generate an acid when exposed to a light, can be used. The non-limiting examples of the PAG include onium salts such as sulfonium salts or iodonium salts. Specifically, the PAG is selected from a group consisting of phthalimidotrifluoromethane sulfonate, dinitrobenzyltosylate, n-decyl disulfone and naphthylimido trifluoromethane sulfonate. Also, the PAG is selected from the group consisting of diphenyl iodonium triflate, diphenyl iodonium nonaflate, diphenyl iodonium hexafluorophosphate, diphenyl iodonium hexafluoroarsenate, diphenyl iodonium hexafluoroantimonate, diphenyl p-methoxyphenyl sulfonium triflate, diphenyl p-toluenyl sulfonium triflate, diphenyl p-tert-butylphenyl sulfonium triflate, diphenyl p-isobutylphenyl sulfonium triflate, triphenylsulfonium triflate, tris(p-tert-butylphenyl) sulfonium triflate, diphenyl p-methoxyphenyl sulfonium nonaflate, diphenyl p-toluenyl sulfonium nonaflate, diphenyl p-tert-butylphenyl sulfonium nonaflate, diphenyl p-isobutylphenyl sulfonium nonaflate, triphenylsulfonium nonaflate, tris(p-tert-butylphenyl) sulfonium nonaflate, triphenylsulfonium hexafluoroarsenate, triphenylsulfonium hexafluoroantimonate, triphenylsulfonium triflate and dibutylnaphtylsulfonium triflate.

The amount of the base compound, if used, is 0.01 to 10 weight parts, preferably 1 to 2 weight parts with respect to 100 weight parts of the photosensitive molecular compound or 100 weight part of sum of the photosensitive molecular compound and the conventional photosensitive polymer. Wherein, if the amount of the base compound is too little (less than 0.01 wt %), it is not easy to control a diffusion of the acid generated in an exposure process so that the pattern profile is uneven. If the amount of the base compound is too much (more than 10 weight parts), the diffusion of the acid generated is suppressed so that pattern is not easily formed. Also, as the base compound which is used as quencher or reaction inhibitor, the conventional quenchers or reaction inhibitors, for example, organic bases such as tri-ethylamine, trioctylamine, tri-iso-butylamine, tri-iso-octylamine, di-ethanolamine, tri-ethanolamine and mixture thereof, can be used without limitation. The surfactant, at need, is added in the present photoresist composition so as to improve a mixing uniformity of the photoresist composition, coating property of the photoresist composition and developing property of the photoresist film after the light exposure. As the surfactant, conventional various surfactant used in the photoresist composition can be used. Exemplarily surfactants include, but are not limited to, fluorine-based surfactant or fluorine-silicon-based surfactant. The amount of the surfactant is 0.001 to 2 weight parts, preferably 0.01 to 1 weight parts with respect to solid content 100 weight parts of the photoresist composition. If the amount of the surfactant is too little, function of surfactant does not sufficiently work, and if the amount of the surfactant is too much, the resist property such as shape stability or a storage stability of the composition except for the coating property, may be adversely affected.

As the organic solvent, the conventional various organic solvents for the photoresist composition can be used. Exemplary organic solvents include, but are not limited to, ethyleneglycol monomethylethyl, ethyleneglycol monoethylether, ethyleneglycol monomethylether, ethyleneglycol monoacetate, diethylene glycol, diethyleneglycol monoethylether, propyleneglycol monomethyletheracetate (PGMEA), propyleneglycol, propyleneglycol monoacetate, toluene, xylene, methylethylketone, methyl isoamyl ketone, cyclohexanone, dioxane, methyl lactate, ethyl lactate, methyl pyruvate, ethyl pyruvate, methyl methoxy propionate, ethyl ethoxy propionate, N,N-dimethylformamide, N,N-dimethylacetamide, N-methyl-2-pyrollidone, 3-ethoxy ethyl propionate, 2-heptanone, gamma-butyrolactone, ethyl 2-hydroxy propionate, ethyl 2-hydroxy-2-methyl propionate, ethoxyethyl acetate, hydroxylethyl acetate, methyl 2-hydroxy-3-methylbutanoate, methyl 3-methoxy-2-methylpropionate, ethyl 3-ethoxy propionate, ethyl 3-methoxy-2-methyl propionate, ethyl acetate, butyl acetate, and mixture thereof.

In order to form a photoresist pattern with the photoresist composition according to the present invention, the following conventional photolithography process can be carried out. First, the photoresist is applied or coated on a substrate such as silicon wafer, an aluminum substrate, and so on, for example, with a spin coater to form a photoresist layer. The photoresist layer is exposed to a light of a predetermined pattern. After the exposure, if necessary, the photoresist pattern is thermally treated (heated), which is called as PEB (Post Exposure Bake), and is developed to form the photoresist pattern. The exposure process is carried out using ArF (193 nm), KrF (248 nm), F2 (157 nm), EUV (Extreme Ultra Violet, 13.5 nm), VUV (Vacuum Ultra Violet), E-beam, X-ray, Immersion lithography or ion beam. As the developing solution for the developing process, an alkali aqueous solution including an alkali compound such as sodium hydroxide, potassium hydroxide, sodium carbonate, tetramethylammonium hydroxide (TMAH) of the concentration of 0.1 to 10 weight % can be used. If necessary, the developing solution may further include water-soluble organic solvent such as methanol, ethanol, and a surfactant of a proper amount. Also, after the developing, the substrate is further washed with ultra pure water.

Hereinafter, detailed description of the present invention will be made through the examples and comparative examples. The preferable examples are provided for better understanding of the present invention. However, the present invention is not limited by the following examples.

Examples 1-1 to 1-7

Preparation of Photosensitive Molecular Compound

A. Preparation of Intermediate Represented by Formula 3
As shown in following Table 1, benzene derivatives,

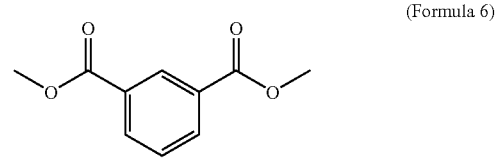

(Formula 6)

was dissolved in 100 ml of ethanol solvent in a reactor, and

(Formula 7-1)

and

(Formula 7-2)

as aldehyde compound were added to the reactor. The reaction solution was stirred while maintaining a temperature of the reactor at 90° C. 30 ml of hydrochloric acid was dropped to the reaction solution and stirred for 48 hours. After a completion of a reaction, 100 ml of cold distilled water was added and the reaction solution was extracted with 200 ml of ethylacetate three times. The extracted solution was dried with magnesium sulfate anhydride and then distilled under the reduced pressure to produce a compound. The compound produced was re-crystallized with diethylether to obtain an intermediate of Formula 3.

TABLE 1

| Reaction | Benzene derivatives and amount used (g) | Aldehyde compound and amount used (g) | Yield |
|---|---|---|---|
| Reaction 1 | Formula 6, 9.7 g (0.05 mole) | Formula 7a, 1.5 g (0.05 mole) | 83% |
| Reaction 1 | Formula 6, 9.7 g (0.05 mole) | Formula 7b, 2.2 g (0.12 mole) | 79% |

$^1$H-NMR data of the obtained compound are as follows.

$^1$H-NMR (CDCl$_3$, internal standard) of compound represented by Formula 3 (R$_1$: H): δ (ppm) 8.32 (CH, 4H), 7.06 (CH, 4H), 4.06 (CH$_2$, 8H), 3.92 (CH$_3$, 24H).

$^1$H-NMR (CDCl$_3$, internal standard) of compound represented by Formula 3 (R$_1$: methyl group): δ (ppm) 8.42 (CH, 4H), 7.10 (CH, 4H), 4.35 (CH, 4H), 3.94 (CH$_3$, 24H) 1.68 (CH$_3$, 12H).

B. Preparation of Intermediate Represented by Formula 4

As shown in following Table 2, the intermediate obtained at the above step A, represented by Formula 3 and a solvent of aqueous sodium hydroxide (NaOH) saturated solution were added to a reactor, and the reaction solution was stirred for 24 hours while maintaining the temperature of the reactor at 40° C. After the completion of the reaction, the temperature of the reactor was dropped to room temperature and the reactant was extracted with 200 ml of ethylacetate three times. The extracted solution was dried with magnesium sulfate anhydride and then distilled under the reduced pressure to produce a compound. The compound produced was re-crystallized with acetone to obtain an intermediate of Formula 4.

TABLE 2

| Reaction | Compound of Formula 3 and amount used (g) | aqueous NaOH saturated solution and amount used (g) | Yield |
|---|---|---|---|
| Reaction 2 | Formula 3 (R$_1$: H), 8.2 g (0.01 mole) | 40 g | 95% |
| Reaction 2 | Formula 3 (R$_1$: methyl group), 8.8 g (0.01 mole) | 40 g | 97% |

$^1$H-NMR data of the obtained compound are as follows.

$^1$H-NMR (CDCl$_3$, internal standard) of compound represented by Formula 4 (R$_1$: H): δ (ppm) 11.84 (OH, 8H), 8.52 (CH, 4H), 7.21 (CH, 4H), 4.02 (CH2, 8H).

$^1$H-NMR (CDCl$_3$, internal standard) of compound represented by Formula 4 (R$_1$: methyl group): δ (ppm) 11.83 (OH, 8H), 8.64 (CH, 4H), 7.23 (CH, 4H), 4.31 (CH, 4H), 1.65 (CH$_3$, 12H).

C. Preparation of Intermediate Represented by Formula 5

As shown in following Table 3, the intermediate obtained at the above step B, represented by Formula 4 was dissolved in 100 ml of THF anhydride in a reactor and the temperature of the reactor was lowered at 0° C. Thionyl chloride (SOCl$_2$) was slowly dropped to the reactor, the temperature of the reactor was raised to the room temperature and the reaction was performed for 6 hours. After the completion of the reaction, the solvent and unreacted thionyl chloride were removed by distilling under the reduced pressure, and the remainder was re-crystallized with diethylether to obtain an intermediate of Formula 5.

TABLE 3

| Reaction | Compound of Formula 4 and amount used (g) | Amount used of SOCl$_2$ | Yield |
|---|---|---|---|
| Reaction 3 | Formula 4 (R$_1$: H), 7.1 g (0.01 mole) | 11.7 g (0.1 mole) | 76% |
| Reaction 3 | Formula 4 (R$_1$: methyl group), 7.7 g (0.01 mole) | 11.7 g (0.1 mole) | 71% |

$^1$H-NMR data of the obtained compound are as follows.

$^1$H-NMR (CDCl$_3$, internal standard) of compound represented by Formula 5 (R$_1$: H): δ (ppm) 8.60 (CH, 4H), 7.31 (CH, 4H), 4.09 (CH$_2$, 8H).

$^1$H-NMR (CDCl$_3$, internal standard) of compound represented by Formula 5 (R$_1$: methyl group): δ (ppm) 8.73 (CH, 4H), 7.35 (CH, 4H), 4.34 (CH, 4H), 1.69 (CH$_3$, 12H).

D. Preparation of Photosensitive Molecular Compounds Represented by Formulas 2a to 2g As shown in following Table 4, the intermediate obtained at the above step C, represented by Formula 5 was dissolved in an organic salt of pyridine and then -continued

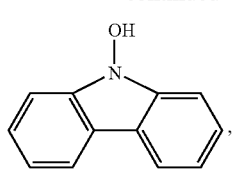
(Formula 8f)

as an oxime derivative compound were slowly dropped respectively through a solid addition funnel at room temperature. After dropping the oxime derivatives, the reaction was performed at room temperature for 12 hours. After the reaction, the reactant was filtered and the obtained solid compound was washed with water several times to prepare photoresist molecular compounds represented by Formula 2a to Formula 2g.

TABLE 4

| Example | Reaction | Compound of Formula 5 and amount used | Oxime derivative compound and amount used | Yield |
|---|---|---|---|---|
| 1-1 | Reaction 4 | Formula 5 (R1: H) 8.6 g (0.01 mol) | Formula 8a 10.2 g (0.09 mol) | 65% |
| 1-2 | Reaction 4 | Formula 5 (R1: H) 8.6 g (0.01 mol) | Formula 8b 14.9 g (0.09 mol) | 56% |
| 1-3 | Reaction 4 | Formula 5 (R1: H) 8.6 g (0.01 mol) | Formula 8c 12.2 g (0.09 mol) | 71% |
| 1-4 | Reaction 4 | Formula 5 (R1: H) 8.6 g (0.01 mol) | Formula 8d 14.7 g (0.09 mol) | 61% |
| 1-5 | Reaction 4 | Formula 5 (R1: H) 8.6 g (0.01 mol) | Formula 8a 19.2 g (0.09 mol) | 62% |
| 1-6 | Reaction 4 | Formula 5 (R1: H) 8.6 g (0.01 mol) | Formula 8e 16.5 g (0.09 mol) | 48% |
| 1-7 | Reaction 4 | Formula 5 (R1: methyl group) 9.1 g (0.01 mol) | Formula 8a 10.2 g (0.09 mol) | 59% |

$^1$H-NMR data of the obtained photosensitive molecular compound are as follows.

$^1$H-NMR (CDCl$_3$, internal standard) of compound represented by Formula 2a: δ (ppm) 8.88 (CH, 4H), 7.30 (CH, 4H), 4.12 (CH$_2$, 8H), 1.59 (CH$_2$, 32H), 1.27 (CH$_2$, 16H). 1.20 (CH$_2$, 32H)

$^1$H-NMR (CDCl$_3$, internal standard) of compound represented by Formula 2b: δ (ppm) 8.85 (CH, 4H), 7.31 (CH, 4H), 4.10 (CH$_2$, 8H), 1.74 (CH$_2$, 16H), 1.44 (CH$_2$, 48H). 1.21 (CH, 16H), 1.08 (CH$_2$, 32H).

$^1$H-NMR (CDCl$_3$, internal standard) of compound represented by Formula 2c: δ (ppm) 8.89 (CH, 4H), 7.76 (CH, 16H), 7.34 (CH, 4H), 7.28 (CH, 24H), 4.09 (CH$_2$, 8H), 1.91 (CH$_3$, 24H).

$^1$H-NMR (CDCl$_3$, internal standard) of compound represented by Formula 2d: δ (ppm) 8.86 (CH, 4H), 8.15 (CH, 16H), 7.60 (CH, 16H), 7.30 (CH, 4H), 4.12 (CH$_2$, 8H).

$^1$H-NMR (CDCl$_3$, internal standard) of compound represented by Formula 2e: δ (ppm) 8.88 (CH, 4H), 8.04 (CH, 16H), 7.97 (CH, 16H), 7.87 (CH, 16H), 7.31 (CH, 4H), 4.10 (CH$_2$, 8H).

$^1$H-NMR (CDCl$_3$, internal standard) of compound represented by Formula 2f: δ (ppm) 8.85 (CH, 4H), 7.69 (CH, 16H), 7.50 (CH, 16H), 7.41 (CH, 16H), 7.32 (CH, 4H), 7.02 (CH, 16H), 4.11 (CH$_2$, 8H).

$^1$H-NMR (CDCl$_3$, internal standard) of compound represented by Formula 2g: δ (ppm) 8.87 (CH, 4H), 7.36 (CH, 4H), 4.32 (CH, 4H), 1.72 (CH$_3$, 12H), 1.58 (CH$_2$, 32H), 1.25 (CH$_2$, 16H), 1.21 (CH$_2$, 32H).

Manufacturing Example

Preparation of Photoresist Polymer Represented by Formula 9

8.89 g (0.04 mol) of 9-methacryloyloxy-4-oxa-tricyclo[5.2.1.02,6]decan-3-one, 23.4 g (0.1 mol) of 2-methyl-2-adamanthyl methacrylate, 11.8 g (0.05 mol) of 1-methacryloyloxy-3-hydroxyadamantan and 0.7 g of azobis (isobutyronitrile) (AIBN) were added to a reactor, and then they were dissolved in 100 g of THF anhydride. Gas was removed from the solution (reactant) by using ampoule as a freezing method and the reactant from which the gas was removed was polymerized at 68° C. for 24 hours. After the polymerization, the reactant was slowly dropped to an excess of diethylether to be precipitated and again the precipitated was dissolved in THF. The reactant dissolved was re-precipitated with diethylether to prepare a polymer represented by Formula 9 (wherein, a, b and c are mol % of each repeating unit with respect to total repeating unit composing the polymer, and is proportional to an amount of each monomer used in a polymerization reaction.). The synthesized polymer was analyzed through GPC (Gel permeation chromatography). The weight average molecular weight (Mw) of synthesized polymer was 9,201, the number-average molecular weight (Mn) of synthesized polymer was 5,124, and polydispersity (PD) of synthesized polymer was 1.80.

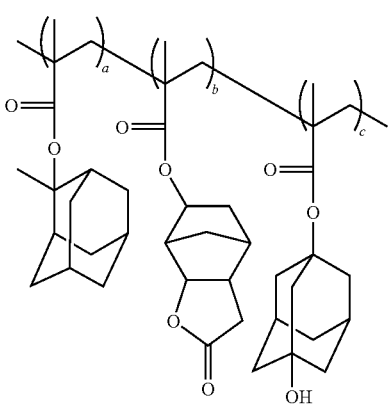

[Formula 9]

Example 2-1 to Example 2-7 and Comparative Example 1

Preparation of the Photoresist Composition

The photosensitive molecular compound prepared in each of Examples 1-1 to 1-7 (Formula 2a to Formula 2g) and triethanolamine (TEOA) as an organic salt were completely dissolved in 17 g of propylene glycol monomethyl ether acetate (PGMEA) and were filtered by 0.2 μm of disk filter, to prepare the photoresist compositions (Example 2-1 to Example 2-7). While, 2.0 g of photoresist polymer prepared at the manufacturing example (Formula 9), 0.014 g of triethanolamine (TEOA) and 0.08 g of triphenylsulformium triflate were completely dissolved in 17 g of propylene glycol monomethyl ether acetate (PGMEA) and were filtered by 0.2 μm of disk filter to prepare the photoresist composition (Comparative Example 1). The kind and amount of the photoresist composition which were used in these Examples and Comparative Example 1 are shown in following Table 5.

TABLE 5

|  | Photoresist compound and amount used | Amount of PAG (triphenylsulfornium triflate) | Amine compound and amount used | Organic solvent |
|---|---|---|---|---|
| Example 2-1 | Formula 2a, 2.0 g | — | TEOA, 0.014 g | PGMEA, 17 g |
| Example 2-2 | Formula 2b, 2.0 g | — | TEOA, 0.014 g | PGMEA, 17 g |
| Example 2-3 | Formula 2c, 2.0 g | — | TEOA, 0.014 g | PGMEA, 17 g |
| Example 2-4 | Formula 2d, 2.0 g | — | TEOA, 0.014 g | PGMEA, 17 g |
| Example 2-5 | Formula 2e, 2.0 g | — | TEOA, 0.014 g | PGMEA, 17 g |
| Example 2-6 | Formula 2f, 2.0 g | — | TEOA, 0.014 g | PGMEA, 17 g |
| Example 2-7 | Formula 2g, 2.0 g | — | TEOA, 0.014 g | PGMEA, 17 g |
| Comparative Example 1 | Formula 9, 2.0 g | 0.08 g | TEOA, 0.014 g | PGMEA, 17 g |

Example 3-1 to Example 3-7 and Comparative Example 2

Formation of Photoresist Pattern

The photoresist composition prepared in the Examples 2-1 to 2-7 and Comparative Example 1 were spin coated on the upper parts of the to-be-exposed layer of silicon wafers being treated in hexamethyl disiloxane (HMDS) with 0.1 μm thickness to prepare a thin-film of photoresist. The photoresist layer was pre-baked at a temperature of 100° C. (or 120° C.) for 90 seconds in a oven or on a hot plate, and was exposed with a KrF laser apparatus having numerical aperture of 0.5 under optical exposure energy (EOP), and then was post-baked at a temperature of 100° C. (or 120° C.) for 90 seconds. Thereafter, the baked wafer was developed with 2.38 weight % of tetra-methylammonium hydroxide (TMAH) aqueous solution for about 30 seconds to form a uniform line/space pattern of 0.2 μm. Line width variations of the obtained pattern were measured and are set forth in the following Table 6.

TABLE 6

|  | Resolution (nm) | Line width variation (nm) |
|---|---|---|
| Example 3-1 (Formula 2a) | 200 | 2.5 |
| Example 3-2 (Formula 2b) | 200 | 2.8 |
| Example 3-3 (Formula 2c) | 200 | 3.0 |
| Example 3-4 (Formula 2d) | 200 | 2.8 |
| Example 3-5 (Formula 2e) | 200 | 3.5 |
| Example 3-6 (Formula 2f) | 200 | 3.5 |
| Example 3-7 (Formula 2g) | 200 | 3.2 |
| Comparative Example 2 (Formula 9) | 200 | 4.5 |

As shown in Table 6, the photoresist compositions (Example 3-1 to Example 3-7) including the photosensitive molecular compound of the present invention have good linewidth stability compared to the photoresist composition including the conventional chemically amplified photosensitive polymer (Comparative Example 2). Also, 1:1 line/space pattern having 50 nm of linewidth can be successfully formed by using a photosensitive composition of the present invention, AIXUV of EUV exposure instrument polymer and 13.5 nm (EUV) of a light source.

The invention claimed is:

1. A photosensitive molecular compound having a structure of the following Formula 1,

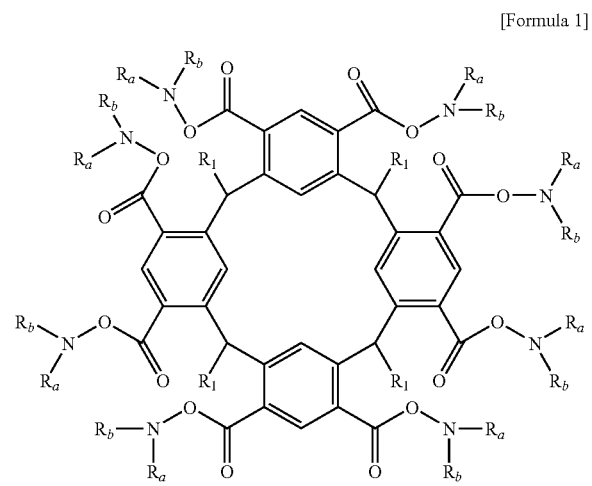

[Formula 1]

in Formula 1, $R_1$ is hydrogen atom or methyl group ($CH_3$); wherein i) $R_a$ and $R_b$ each is independently alkyl group of 1-6 carbon atoms, alkylcarbonyl group of 2-7 carbon atoms, aryl group of 6-10 carbon atoms or arylcarbonyl group of 7-11 carbon atoms, or ii) $R_a$ and $R_b$ are combined as a single group which is doubly bonded to nitrogen atom, and wherein said single group is an alkyl or cycloalkyl group of 1-20 carbon atoms or arylalkyl group of 7-20 carbon atoms, or iii) $R_a$ and $R_b$ each is independently alkyl group of 1-6 carbon atoms, alkylcarbonyl group of 2-7 carbon atoms, aryl group of 6-10 carbon atoms or arylcarbonyl group of 7-11 carbon atoms and wherein $R_a$ and $R_b$ combine with the nitrogen atom to form a ring.

2. The photosensitive molecular compound of claim 1, wherein $R_a$ and $R_b$ are coupled to each other to form a ring structure.

3. The photosensitive molecular compound of claim 1, wherein said photosensitive molecular compound is selected from a group consisting of

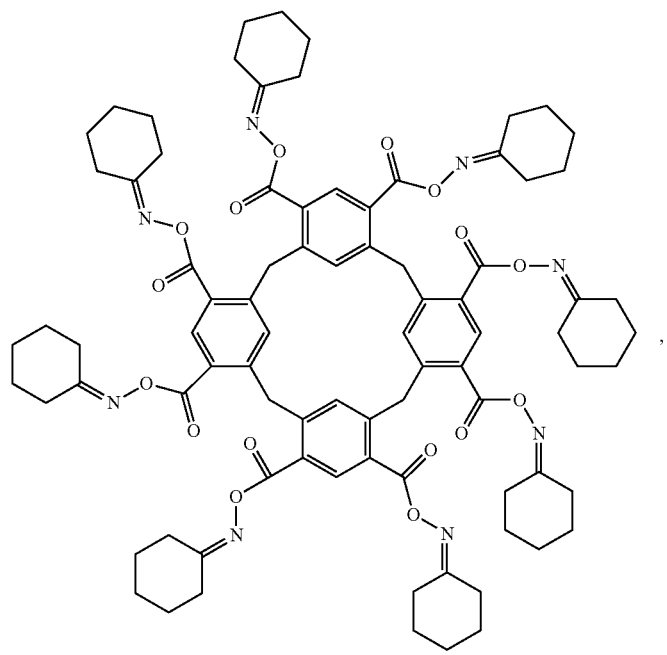
,
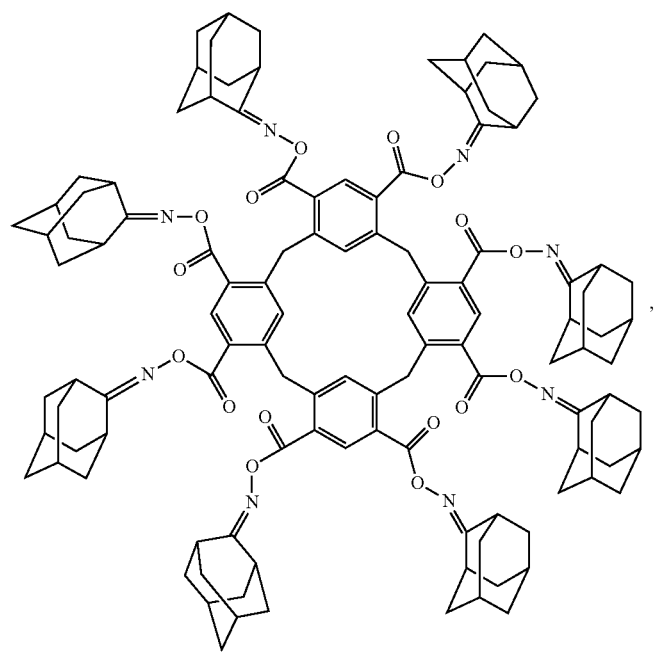
,

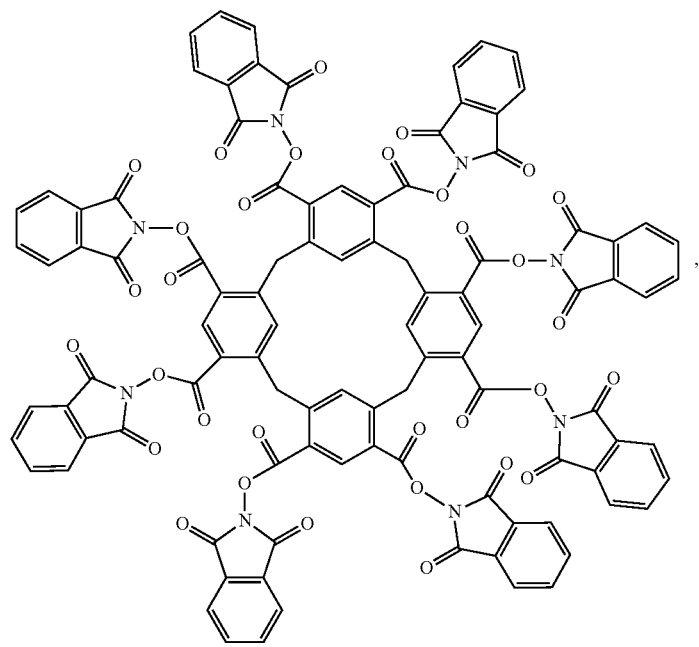
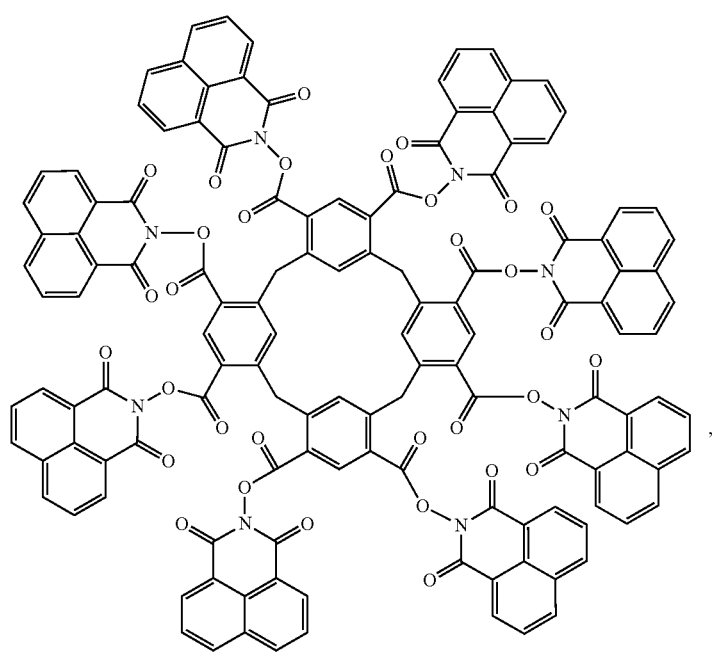

-continued
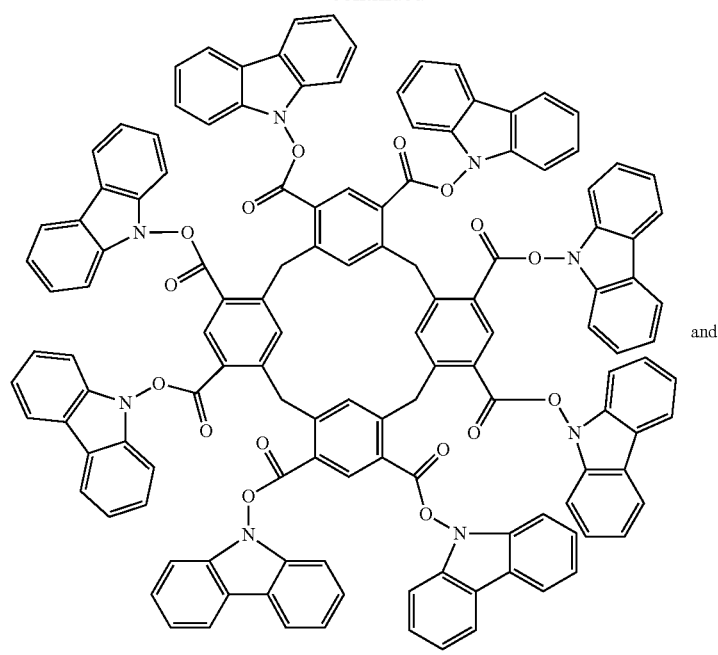
and
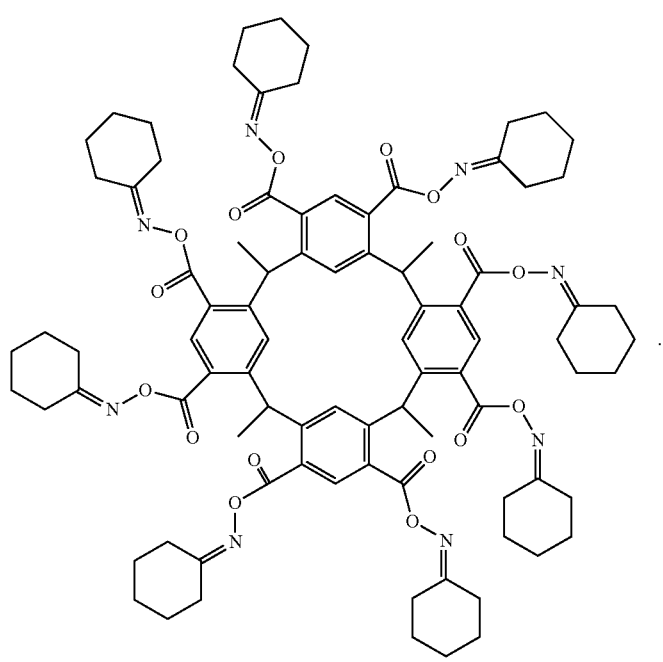

4. A photosensitive molecular compound having the following structure

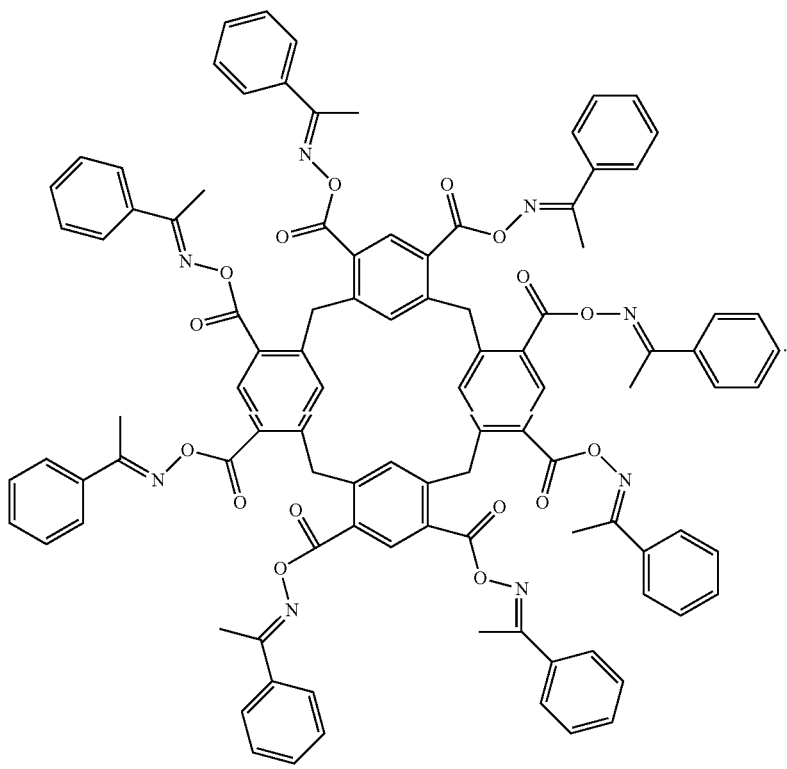

5. A photoresist composition comprising:

1 to 85 wt % (weight %) of photosensitive molecular compound having a structure of the following Formula 1,

[Formula 1]

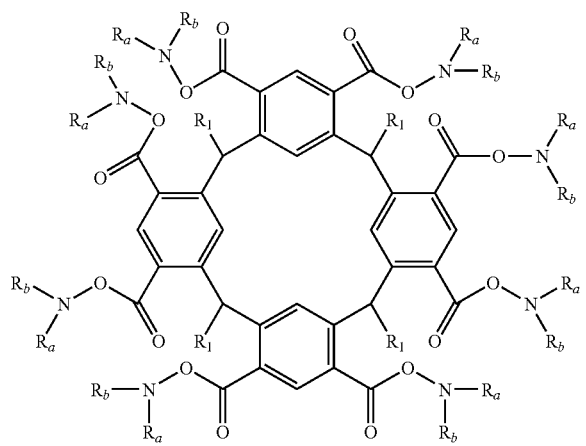

in Formula 1, $R_1$ is hydrogen atom or methyl group ($CH_3$); wherein i) $R_a$ and $R_b$ each is independently alkyl group of 1-6 carbon atoms, alkylcarbonyl group of 2-7 carbon atoms, aryl group of 6-10 carbon atoms or arylcarbonyl group of 7-11 carbon atoms, or ii) $R_a$ and $R_b$ are combined as a single group which is doubly bonded to nitrogen atom, and wherein said single group is an alkyl or cycloalkyl group of 1-20 carbon atoms or arylalkyl group of 7-20 carbon atoms, or iii) $R_a$ and $R_b$ each is independently alkyl group of 1-6 carbon atoms, alkylcarbonyl group of 2-7 carbon atoms, aryl group of 6-10 carbon atoms or arylcarbonyl group of 7-11 carbon atoms and wherein $R_a$ and $R_b$ combine with the nitrogen atom to form a ring; and a remaining organic solvent.

6. The photoresist composition of claim 5, further comprising 0.01 to 10 weight parts of a base compound with respect to 100 weight parts of the photosensitive molecular compound, wherein, the base compound is selected from a group of consisting of tri-ethylamine, tri-octylamine, tri-iso-butylamine, tri-iso-octylamine, di-ethanolamine, tri-ethanolamine and mixture thereof.

7. A method for forming a photoresist pattern, comprising the step of:

a) coating a photoresist composition on a substrate to form a photoresist layer;

b) exposing the photoresist layer to a light;

c) heating the exposed photoresist layer; and d) developing the heated photoresist layer to form the photoresist pattern, wherein the photoresist composition comprises i) 1 to 85 wt % (weight %) of photosensitive molecular compound having a structure of the following Formula 1,

[Formula 1]

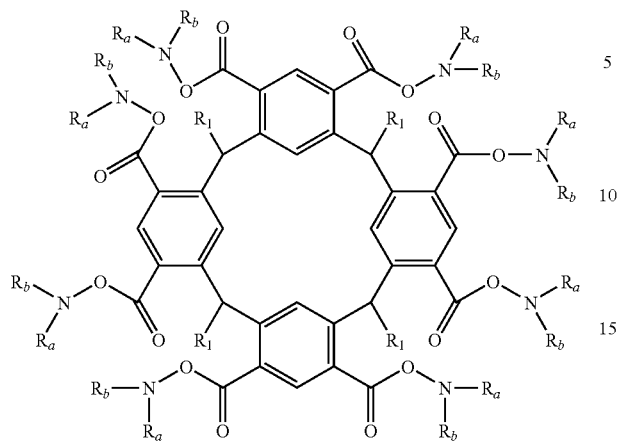

in Formula 1, $R_1$ is hydrogen atom or methyl group ($CH_3$); wherein

A) $R_a$ and $R_b$ each is independently alkyl group of 1-6 carbon atoms, alkylcarbonyl group of 2-7 carbon atoms, aryl group of 6-10 carbon atoms or arylcarbonyl group of 7-11 carbon atoms, or B) $R_a$ and $R_b$ are combined as a single group which is doubly bonded to nitrogen atom, and wherein said single group is an alkyl or cycloalkyl group of 1-20 carbon atoms or arylalkyl group of 7-20 carbon atoms, or C) $R_a$ and $R_b$ each is independently alkyl group of 1-6 carbon atoms, alkylcarbonyl group of 2-7 carbon atoms, aryl group of 6-10 carbon atoms or arylcarbonyl group of 7-11 carbon atoms and wherein $R_a$ and $R_b$ combine with the nitrogen atom to form a ring; and ii) an organic solvent.

* * * * *